(12) United States Patent
Bodenmiller

(10) Patent No.: US 7,234,938 B2
(45) Date of Patent: Jun. 26, 2007

(54) MILLING/GRINDING MACHINE FOR THE MANUFACTURE OF DENTAL-MEDICAL WORKPIECES

(75) Inventor: Anton Bodenmiller, Leutkirch (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 290 days.

(21) Appl. No.: 10/106,770

(22) Filed: Mar. 26, 2002

(65) Prior Publication Data

US 2002/0137002 A1 Sep. 26, 2002

(30) Foreign Application Priority Data

Mar. 26, 2001 (DE) .......................... 201 05 248 U

(51) Int. Cl.
*A61C 3/06* (2006.01)
(52) U.S. Cl. .................................... 433/51
(58) Field of Classification Search ................ 433/51, 433/76, 49; 264/16, 17, 18; 408/44, 45; 269/287, 288, 71, 73, 46, 47, 126
See application file for complete search history.

(56) References Cited

U.S. PATENT DOCUMENTS

| 1,490,191 | A | * | 4/1924 | Allcutt | ..................... 219/95 |
| 4,121,817 | A | * | 10/1978 | Pavlovsky | ................. 269/296 |
| 4,411,626 | A | * | 10/1983 | Becker et al. | ............. 433/223 |
| 4,459,190 | A | * | 7/1984 | Inoue | ..................... 205/654 |
| 4,833,764 | A | * | 5/1989 | Muller | ......................... 29/40 |
| 4,856,234 | A | * | 8/1989 | Goins | .......................... 451/42 |
| 5,135,393 | A |   | 8/1992 | Eidenbenz et al. | ........... 433/53 |
| 5,383,752 | A | * | 1/1995 | Rheinberger et al. | ....... 409/105 |
| 6,261,098 | B1 | * | 7/2001 | Persson | ..................... 433/213 |

FOREIGN PATENT DOCUMENTS

| DE | 199 30 564 A1 | 7/1999 |
| EP | 0 391 446 A1 | 4/1990 |
| EP | 0 455 853 A1 | 5/1990 |
| WO | WO 98/36871 | 8/1998 |
| WO | WO 00/62705 | * 10/2000 |

* cited by examiner

*Primary Examiner*—Melba Bumgarner
(74) *Attorney, Agent, or Firm*—Marshall, Gerstein & Borun LLP

(57) ABSTRACT

The invention relates to a milling/grinding machine for the manufacture of dental-medical or dental-technical workpieces, having a workpiece receiver (3) and a tool (7) which can be moved, with respect to a workpiece (1) arranged in the workpiece receiver (3), linearly along three axes (X, Y, Z) standing perpendicularly of one another. In order to provide a milling/grinding machine for highly exact and economic manufacture of medical, dental-medical and dental-technical prosthetic parts for the medical technician, dentist, dental assistant and the dental technician directly in the medical laboratory, practice or commercial laboratory, the tool (7) and the workpiece receiver (3) are each arranged rotatably and/or pivotably.

13 Claims, 3 Drawing Sheets

MILLING/GRINDING MACHINE FOR THE MANUFACTURE OF DENTAL-MEDICAL WORKPIECES

TECHNICAL FIELD

The present invention relates to a milling/grinding machine for the manufacture of workpieces of dental materials.

DESCRIPTION OF RELATED ART

In medical technology, dental medicine and dental technology, prosthetic parts are manufactured of high-value noble metal alloys, cobalt chromium alloys, titanium, ceramics and plastics. The production of such prosthetic works is effected for the most part using molding processes. For reasons of biocompatibility, however, in the meantime, in the event of appropriate indications, prosthetic frameworks are also manufactured using galvanic processes or as ceramics caps, and then additionally ceramically coated.

The manufacture of dentures by means of CAD/CAM systems is in the meantime used in some individual cases, but to date has not been able to achieve the expected level of use because of various technical problems, system components which are difficult for the dental technician to master, and the high system costs. Thereby there has primarily been realized the grinding of inlays and onlays out of glass ceramics blocks.

A CAD/CAM system for the manufacture of ceramics caps has in the meantime been developed by the firm Espe Dental AG under the designation Lava. Thereby, a model of the tooth stump is first measured three dimensionally, and the structure of a suitable cap calculated under computer control. On the basis of this data a milling program for a milling machine is calculated, which milling machine mills from a green body a blank of the desired structure. This green body is pre-sintered zirconium oxide, which in comparison to completely sintered material is substantially softer. The blank manufactured in this manner is then sintered to a high strength ceramics workpiece.

A further process for the manufacture of medical, dental-medical, dental-technical and technical parts of ceramics is described in DE 199 30 564 A1 belonging to the present applicant. Here also a milling program for working the workpiece from a blank is calculated on the basis of an optically measured model. Thereby, the blank consists of a powder-like ceramics raw material which is pressed to a block-like green compact. This has the advantage that in comparison to ceramics blocks which have already been sintered, working can be carried out substantially more easily, quickly and with less abrasion wear of the tool.

Further, excess raw material, which is milled off upon working of the ceramics green compact, can be recovered and used again. There are used as raw material for example the already known and often employed ceramics zirconium oxide ($ZrO_2$) or aluminium oxide ($Al_2O_3$). The use of a $ZrSiO_4$ ceramic is particularly advantageous since upon sintering this shrinks only slightly or not at all.

The machines currently realized for milling ceramics workpieces are, in their structure, based on a classic 3-axis milling machine and therefore are suited only to a limited extent for the demanding free-form surface working of the prosthetic parts. The previous milling/grinding machines thus represent at the present time, from the point of view of the user, one of the most critical factors in the production process for the manufacture of ceramics parts.

A further problem presents itself on the separation of the prosthetic part from the remaining part of the original material block. In this manual separating and grinding procedure there can arise both geometry faults and also in the case of ceramics material ruptures, so that the expensively fabricated part is no longer usable. With a known milling system the workpiece part must, further, be manually rotated by 180, i.e. be re-chucked, for working of the second side. This shifting of the workpiece part in the working space of the machine is connected with risks to accuracy and requires highly precise and thus expensive machine workpiece fixing and changing systems. Additionally a certain ability and exact working by the dental technician are necessary.

SUMMARY OF THE INVENTION

The present invention makes available a milling/grinding machine for the highly precise and economical manufacture of medical, dental-medical and dental-technical prosthetic parts for the medical technician, the dentist, the dental assistant and the dental technician directly in the medical laboratory, practice or commercial laboratory.

According to a preferred embodiment of the invention, a milling/grinding machine has along with a linear movement along three axes standing upon one another, also a rotation and/or pivoting of the tool and the workpiece receiver. During the working, there can be effected a simultaneous control of these five axes of movement, so that also very complex and complicated structures can be worked.

Further preferred embodiments of the invention include the milling/grinding machine having a double spindle, at the ends of which two different tools, e.g. a rough working tool and a fine working tool may be arranged. The double spindle may then for example be rotated on all sides around 180, in order to take up one of the two tools for the working of the workpiece. Also the workpiece receiver can be rotated on all sides around 180, so that without re-chucking, a change can be made from a working of the primary side to a working of the secondary side. Furthermore an auxiliary device can be provided by means of which the surface of the workpiece can be finished.

The milling/grinding machine in accordance with the preferred embodiments of the invention is particularly suitable for the working of ceramics materials for the manufacture of dental-medical or dental-technical workpieces, but however other materials can also be worked.

BRIEF DESCRIPTION OF THE DRAWINGS

In the following the preferred embodiments of the invention will described in more detail with reference to the accompanying drawings, which show.

DETAILED DESCRIPTION OF THE DRAWINGS

The function of the milling/grinding machine in accordance with a preferred embodiment of the invention will be described below on the basis of a description of a process for the manufacture of a ceramics crown. It is however to be noted that the manufacture of workpieces also of other materials is possible.

First, there is produced by the dental technician a saw cut model of plaster or another suitable modelling material on the basis of an impression, as the basis for a prosthetic workpiece. The cement gap necessary for later attachment of the workpiece to the tooth stump may be set for example by means of a corresponding distance coating on the stump preparation.

The stump is then three dimensionally measured in a measuring device, for example mechanically, optically or in accordance with another procedure. Subsequently, the crown is modelled of wax or another modelling material and placed on the stump. The stump with the crown placed thereon is then measured a further time, so that the exact structure of the crown can be calculated. Alternatively, the ceramics part could also be constructed on a CAD-3D-system.

By means of CAM software, in the following the milling path for the working of the crown inner side and the crown outer side are generated, recalculated with reference to the machine structure and loaded as a milling program into the controller of the milling/grinding machine according to a preferred embodiment of the invention.

If as initial material a ceramics green compact or white compact is used which shrinks upon sintering, in the calculation of the milling program this sinter shrinking must be taken into account by means of a correction factor. This is for example the case if zirconium oxide ($ZrO_2$) or aluminium oxide ($Al_2O_3$) is employed as raw material. Preferably, however, $ZrSiO_4$ ceramics are employed, since these ceramics, produced in a reaction sintering process, have the advantage that with a suitable initial material the structure of the workpiece is identical before and after the sintering. The calculation of the milling program is thereby substantially simplified.

Figure 2:
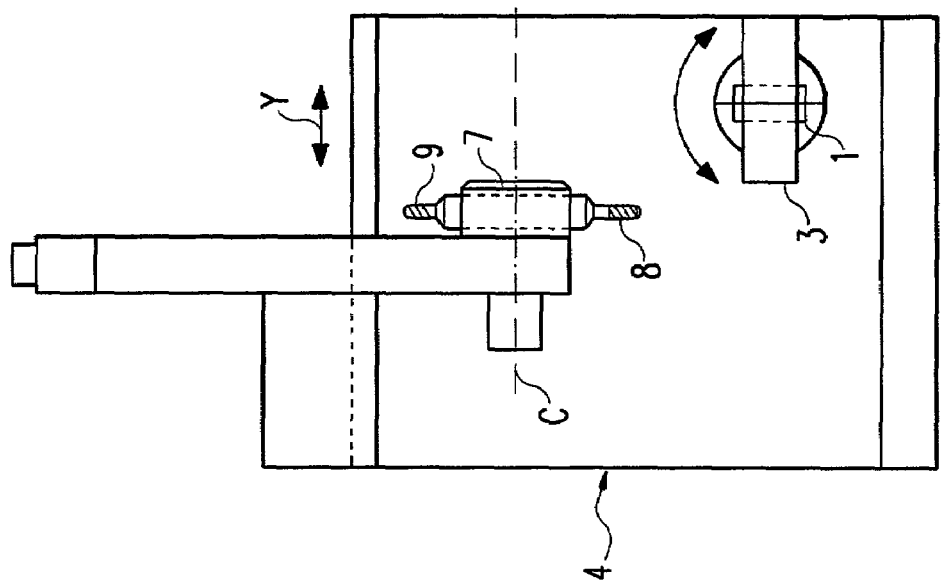
FIG. 2 the milling/grinding machine illustrated in FIG. 1, in a view from the side.
Figure 1:
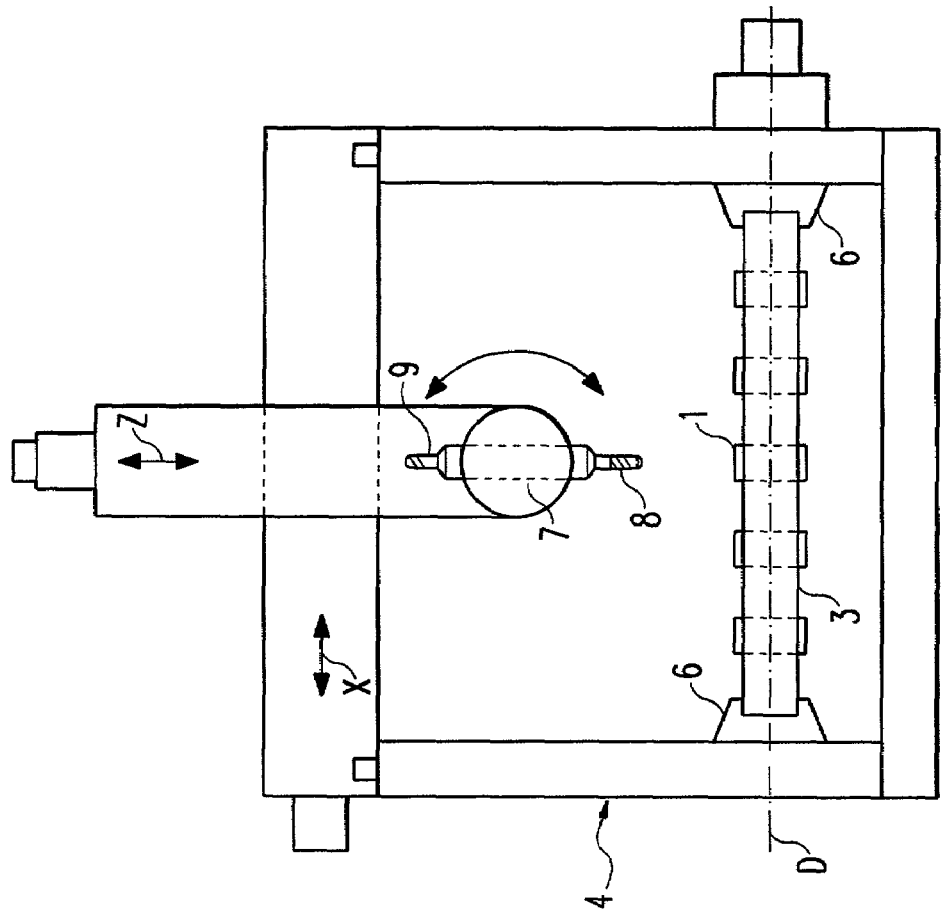
FIG. 1 a milling/grinding machine in a view from the front.
Figure 3:
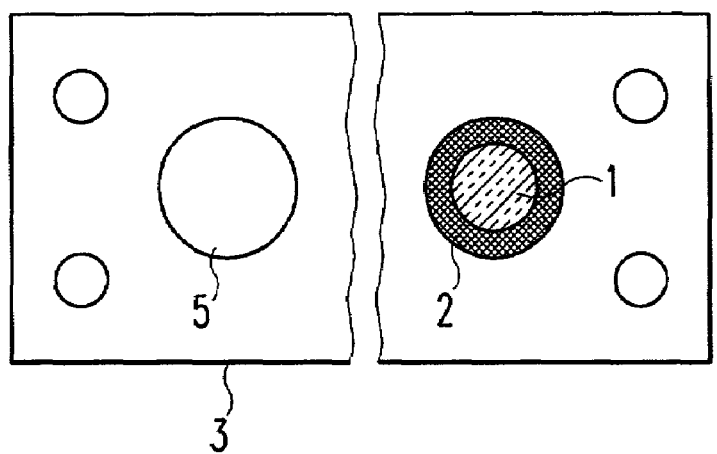
FIG. 3 a workpiece receiver, in a view from above.
Figure 4:
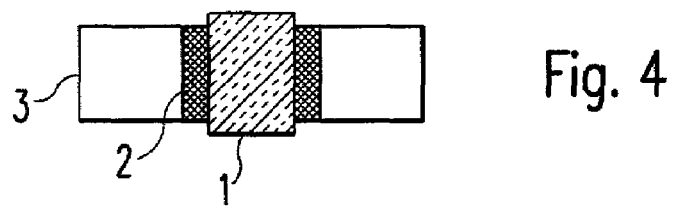
FIG. 4 the workpiece receiver with a ceramic blank placed therein, in section.

In the following working step the ceramics green compact 1 formed by means of compaction of the ceramics raw material, is placed in the workpiece receiver 3 of the milling/grinding machine 4 shown in FIGS. 1 and 2. The workpiece receiver 3, illustrated in FIGS. 3 and 4 in a view from above and in section, consists of an elongate strip which in its longitudinal axis has a plurality of breakthroughs 5 in the form of bores. The fixing of the blank 1 in a bore 5 is thereby effected by means of embedding with a moldable material 2, which fixes the blank 1 reliably, in a form-fitting manner and gently. Depending upon the material be worked or depending upon the working process, there may thereby be employed different embedding materials. In the manufacture of ceramics parts, for example, milling wax is preferred as embedding material.

After placing of the workpiece receiver 3 in the holder 6 of the milling/grinding machine 4 the milling or grinding process is started. The working of the primary side (for example the crown inner side) of the workpiece is thereby effected fully automatically in two steps following directly upon one another, with five simultaneously controlled axes. For this purpose, the tool 7 can be moved linearly along three axes X, Y, Z standing perpendicularly upon one another, and additionally the tool 7 can be rotated and/or pivoted around the axis C and the workpiece receiver 3 can be rotated and/or pivoted around the axis D. These additional pivot axes C and D are perpendicular to one another and each arranged parallel to one of the linear axes X, Y or Z.

Figure 5:
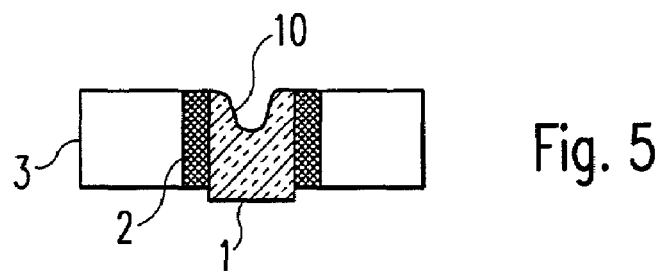
FIG. 5 the workpiece receiver with a blank already partly worked.

The first working step for the working of the primary side consists of rough working, the second of fine working. Thus, the tool consists of a milling/grinding double spindle 7 which is equipped on the one side with a rough working tool 8 and on the other side with a fine working tool 9. For the change from the first to the second working step, the double spindle 7 is pivoted by 180 into its new working position. During the working of the blank 1, the spindle 7 can be pivoted or carried out of its basic position additionally by up to 45 on both sides, so that also very complex structures can be worked of the workpiece. FIG. 5 thereby shows the ceramics blank 1 embedded in the workpiece receiver 3 at a point in time at which the crown inner side 10 has already been worked.

After the end of the automatic working of the primary side this is again molded with an embedding mass, whereby the workpiece receiver 3 is not removed from its holder 6 of the machine 4, so that no re-chucking errors or other inaccuracies arise. This embedding can be effected in particular fully automatically by means of a—not illustrated—embedding device. Then, the tool receiver 3 is pivoted around the axis D by 180 into the second working position, so that the secondary side of the ceramic blank 1 is exactly re-positioned into the new milling position.

As described above, the crown outer side is now also fully automatically rough worked and fine worked from the crown edge to the occlusal surface. Thereby, the D axis of rotation in particular is put to use, around which the receiver 3 is simultaneously pivoted. By means of the prior embedding of the primary side this is reliably held also in this milling procedure of the blank and supported at critical points, so that no material ruptures appear.

After ending of the production process in the milling/grinding machine 4 the workpiece receiver 3 can then be dismounted and the finished workpiece de-embedded. The de-embedding procedure thereby is effected in each case depending upon the kind of embedding material employed. If, for example, milling wax is employed the de-embedding procedure can be effected with the aid of a hot air blower or a special dewaxing apparatus. Here also the possibility arises of re-using the melted off milling wax. The prosthetic workpiece produced in this way can then directly, without finishing of its contours, be completed or sintered.

Figure 7:
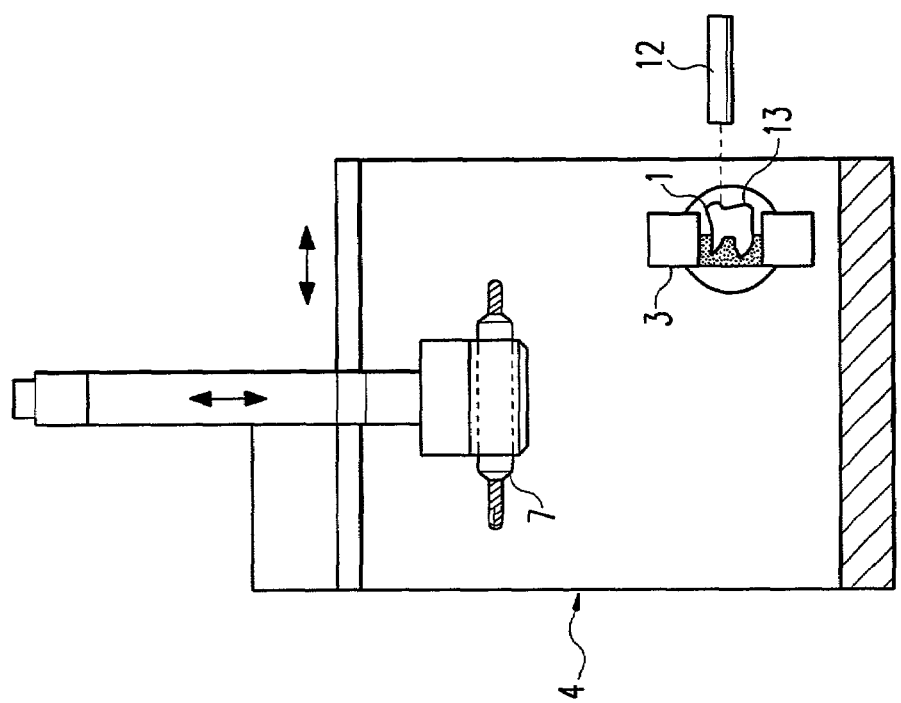
FIG. 7 a second alternate embodiment of a milling/grinding machine.
Figure 6:
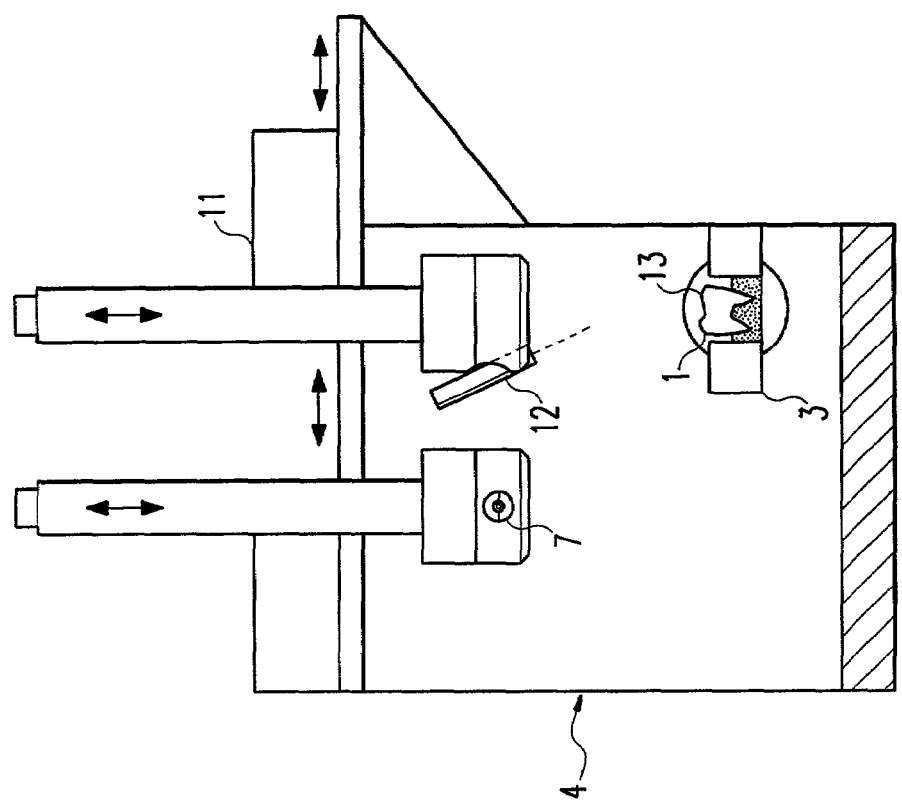
FIG. 6 an alternate embodiment of the milling/grinding machine in a view from the side.

If, on the other hand, a micro-structuring e.g. of the chewing surface is additionally desired, a further working step then takes places which is illustrated in FIG. 6 and 7, which each show an advantageous development of the milling/grinding machine.

In FIG. 6, the milling/grinding machine 4 has alongside the spindle unit 7 an auxiliary device 11 for finishing the chewing surface 13. The finishing is thereby effected—as illustrated—with the aid of a laser 12. Alternatively, other techniques can also be employed for finishing, such as e.g. ultrasonic erosion. Thereby the advantage consists in that the blank 1 need not be removed or re-chucked before this working. Further, the micro-working can likewise be effected on a 5-axis basis, like the preceding milling.

With the alternative illustrated in FIG. 7, the workpiece receiver 3, with the workpiece 1 arranged therein, is rotated by 90, so that the finishing can be carried out by means of an apparatus brought laterally into place, in the present case again by means of a laser 12. A further augmentation of the milling/grinding machine can be effected in that a device is provided by means of which the double spindle 7 is cooled. The wear of the tool for working the workpiece is thereby significantly reduced.

Overall there can thus be economically produced with the milling/grinding machine in accordance with the preferred embodiments of the invention, in medical, dental-medical and dental-technology, implant parts, inlays, partial crowns, crowns, bridges, prosthetic bases and auxiliary parts, exactly and with high mechanical strength suited to the intended purpose, and of various dental materials. A further advantage is that the producer of the prosthetic parts can continue to employ his previous auxiliary work materials, known to him in their processing. It is further possible flexibly exploit the machine capacity through the variable employment possibilities of the machine with regard to workpiece quantities and workpiece dimensions. The consequence thereof is a significant reduction of wasted time and an improved exploitation of the machine capacity and an increase of the process reliability. The employment of the milling/grinding machine is thereby not restricted to the working of ceramics, rather all other dental materials can be worked, whereby due to the 5-axis control also the working of very complex structures is possible.

The invention claimed is:

1. Milling/grinding machine for the manufacture of dental-medical or dental-technical workpieces, comprising a workpiece receiver and a tool which can be moved, with respect to a workpiece arranged in the workpiece receiver, linearly along three axes (X, Y, Z) standing perpendicularly of one another, wherein,
   the tool and the workpiece receiver are each rotatable and/or pivotable; and
   wherein the workpiece receiver has a through-bore including a moldable embedding material disposed within the through-bore for retaining the workpiece within the through-bore, and the through-bore is substantially perpendicular to a pivot axis of the workpiece receiver.

2. Milling/grinding machine according to claim 1, wherein,
   a pivot axis of the tool (C) and the pivot axis of the workpiece receiver (D) are arranged perpendicularly to one another.

3. Milling/grinding machine according to claim 2, wherein,
   the pivot axis of the tool (C) and the pivot axis of the workpiece receiver (D) are each arranged parallel to one of the linear axes (X, Y, Z).

4. Milling/grinding machine according to claim 1, wherein,
   the workpiece receiver is rotatable by at least 180°.

5. Milling/grinding machine according to claim 1, comprising a double spindle having a first tool at a first spindle end and a second tool at a second spindle end, a working position of the double spindle being rotatable.

6. Milling/grinding machine according to claim 5, wherein,
   the working position of the double spindle is rotatable by at least 180°.

7. Milling/grinding machine according to claim 5, wherein,
   the first and second tools comprise a rough working tool and a fine working tool.

8. Milling/grinding machine according to claim 1, wherein,
   the workpiece receiver has a plurality of bores arranged along its longitudinal axis, for receiving workpieces.

9. Milling/grinding machine according to claim 1, comprising an auxiliary device for finishing the workpiece surface.

10. Milling/grinding machine according to claim 9, wherein, the auxiliary device is adjustable with the same degrees of freedom as the tool.

11. Milling/grinding machine according to claim 9, wherein, the auxiliary device is a laser.

12. Milling/grinding machine according to claim 1, comprising an embedding device for the automatic embedding of the workpiece in the workpiece receiver.

13. Milling/grinding machine according to claim 1, comprising a device for cooling the tool.

* * * * *